United States Patent

(12) United States Patent
Commo

(10) Patent No.: US 8,969,407 B2
(45) Date of Patent: Mar. 3, 2015

(54) ADMINISTRATION OF COUMARIN, BUTYLATED HYDROXYANISOLE AND ETHOXYQUINE FOR THE TREATMENT OF CANITIES

(71) Applicant: Stephane Commo, Chaville (FR)

(72) Inventor: Stephane Commo, Chaville (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/689,947

(22) Filed: Nov. 30, 2012

(65) Prior Publication Data

US 2013/0149360 A1   Jun. 13, 2013

Related U.S. Application Data

(62) Division of application No. 11/812,571, filed on Jun. 20, 2007, now Pat. No. 8,344,021.

(60) Provisional application No. 60/819,399, filed on Jul. 10, 2006.

(30) Foreign Application Priority Data

Jun. 20, 2006   (FR) ...................................... 06 52556

(51) Int. Cl.
A61K 31/45   (2006.01)
A61K 8/00    (2006.01)
A61K 8/02    (2006.01)
A61Q 5/00    (2006.01)
A61K 31/47   (2006.01)
A61K 31/05   (2006.01)
A61K 31/075  (2006.01)
A61K 8/49    (2006.01)
A61K 8/34    (2006.01)
A61Q 5/06    (2006.01)

(52) U.S. Cl.
CPC .................. *A61K 8/498* (2013.01); *A61K 8/347* (2013.01); *A61K 8/4926* (2013.01); *A61Q 5/00* (2013.01); *A61Q 5/065* (2013.01)
USPC .......... 514/457; 424/401; 424/70.1; 514/311; 514/718; 514/731

(58) Field of Classification Search
None
See application file for complete search history.

(56) References Cited

U.S. PATENT DOCUMENTS

| | | | | |
|---|---|---|---|---|
| 4,761,288 A * | 8/1988 | Mezei | ........................... | 424/450 |
| 5,292,512 A * | 3/1994 | Schaefer et al. | .............. | 424/401 |
| 5,456,851 A | 10/1995 | Liu et al. | | |
| 5,470,861 A * | 11/1995 | Harmon | ........................ | 514/337 |
| 5,476,852 A * | 12/1995 | Cauwenbergh | .......... | 514/254.07 |
| 5,658,575 A | 8/1997 | Ribier et al. | | |
| 5,958,946 A | 9/1999 | Styczynski et al. | | |
| 6,090,414 A | 7/2000 | Passwater et al. | | |
| 6,316,012 B1 | 11/2001 | N'Guyen et al. | | |
| 2003/0157046 A1 | 8/2003 | Imamura et al. | | |
| 2003/0170193 A1* | 9/2003 | Pate et al. | .................. | 424/70.12 |
| 2003/0185865 A1 | 10/2003 | Jentzsch et al. | | |
| 2003/0215409 A1 | 11/2003 | Quinn et al. | | |
| 2005/0137147 A1* | 6/2005 | Landers et al. | .................. | 514/27 |

FOREIGN PATENT DOCUMENTS

| | | |
|---|---|---|
| EP | 0693278 A2 | 1/1996 |
| EP | 1348421 A2 | 10/2003 |
| FR | 2875403 A1 | 3/2006 |
| JP | 61/238715 | 10/1986 |
| WO | WO 03/059309 A1 | 7/2003 |

OTHER PUBLICATIONS

Aron-Brunetière et al. "Treatment of pityriasis capitis (dandruff) with econzole nitrate," Acta Derm. Venerol. 1977; 57(1): 77-88—abstract only.*
Commo et al., *Human hair graying is linked to specific depletion of hair follicle melanocytes affecting both the bulb and the outer root sheath*, 150 Br. J. of Derm. 435-443 (2004).
European Search Report dated Apr. 28, 2009, issued in European Application No. 07 110 332.
French Search Report issued in corresponding FR 0652556 on May 10, 2007 (2 pages).

* cited by examiner

*Primary Examiner* — Sreeni Padmanabhan
*Assistant Examiner* — Jody Karol
(74) *Attorney, Agent, or Firm* — Buchanan Ingersoll & Rooney PC

(57) ABSTRACT

At least one compound selected from among coumarin and/or derivative thereof, butylated hydroxyanisole, ethoxyquine and mixtures thereof, and admixtures thereof with other active agents selected from among active agents for combating desquamative conditions of the scalp, plant extracts having propigmenting activity and active agents that slow hair loss and/or promote hair regrowth, are useful for preventing and/or limiting and/or stopping the development of canities.

7 Claims, 1 Drawing Sheet

ADMINISTRATION OF COUMARIN, BUTYLATED HYDROXYANISOLE AND ETHOXYQUINE FOR THE TREATMENT OF CANITIES

CROSS-REFERENCE TO RELATED APPLICATIONS

This application is a Divisional Application of U.S. patent application Ser. No. 11/812,571, filed on Jun. 20, 2007, now U.S. Pat No. 8,344,021, which claims priority to U.S. Provisional Patent Application Ser. No. 60/819,399, filed Jul. 10, 2006, which claims priority under 35 U.S.C. §119 of FR 0652556, filed on Jun. 20, 2006 each hereby expressly incorporated by reference in its entirety and each assigned to the assignee hereof.

BACKGROUND OF THE INVENTION

1. Technical Field of the Invention

The present invention relates to the cosmetic administration of coumarin and derivatives thereof, butylated hydroxyanisole and ethoxyquine for treating canities.

2. Description of Background and/or Related and/or Prior Art

The hair follicle is a tubular invagination of the epidermis which extends to the deep layers of the dermis. The lower part, or hair bulb, itself comprises an invagination in which the dermal papilla is located. The lower part of the bulb is an area of cell proliferation where the precursors of the keratinized cells that form hair are found. The ascending cells derived from these precursors become gradually keratinized in the upper part of the bulb, and this assembly of keratinized cells will form the hair shaft.

The color of head hair and of body hair depends especially on the presence, in variable amounts and ratios, of two groups of melanins: eumelanins (brown and black pigments) and pheomelanins (red and yellow pigments). The pigmentation of head hair and body hair requires the presence of melanocytes in the bulb of the hair follicle. These melanocytes are in an active state, that is to say that they synthesize melanins. These pigments are transmitted to the keratinocytes intended to form the hair shaft, which will result in the growth of a pigmented head hair or body hair. This structure is hereinafter called "follicular pigmentation unit".

In mammals, melanogenesis involves at least three enzymes: tyrosinase, DOPAchrome tautomerase (TRP-2, for Tyronsinase Related Protein 2) and DHICA oxidase (TRP-1, for Tyrosinase Related Protein 1).

Tyrosinase is the enzyme that initiates the biosynthesis of melanins. It is also described as being the limiting enzyme of melanogenesis.

TRP-2 catalyzes the tautomerization of DOPAchrome to 5,6-dihydroxyindole-2-carboxylic acid (DHICA). In the absence of TRP-2, the DOPAchrome undergoes a spontaneous decarboxylation to form 5,6-dihydroxyindole (DHI).

DHICA and DHI are both pigment precursors, TRP-1 oxidizes DHICA molecules to form quinine derivatives (Pawelek, J. M. and Chakraborty A. K., "The enzymology of melanogenesis" in "The Pigmentary System: Physiology and Pathophysiology", by Nordlund, J. J., Boissy, R. E., Hearing, V. J., King, R. A., Ortonne, J-P., New York, Oxford University Press, 1998, p. 391-400).

The three enzymes, tyrosinase, TRP-2 and TRP-1, appear to be specifically involved in melanogenesis. In addition, the activity of these three enzymes has been described as being necessary for the maximum activity of biosynthesis of eumelanins.

Head hair and body hair undergo a cycle. This cycle comprises a growth phase (anagen phase), a degenerative phase (catagen phase) and a rest phase (telogen phase) following which a new anagen phase will develop. Due to this hair cycle, and unlike the epidermal pigmentation unit, the follicular pigmentation unit must also be cyclically renewed.

Canities (natural hair whitening) is linked to a specific and gradual depletion of the hair melanocytes that affects both the hair bulb melanocytes and the melanocyte precursor cells (Commo, et al., Br. J. Dermatol., 2004, 150, 435-443). Other cell types present in the haft follicles are not affected. In addition, this depletion of melanocytes is not observed in the epidermis. The cause of this gradual and specific depletion of melanocytes and melanocyte precursors in the hair follicle has not been identified to date.

It therefore appears necessary to combat the disappearance of melanocytes from human hair follicles, a process that affects both the active melanocytes of the bulbs and the quiescent melanocytes of the upper region of the hair follicles, in order to combat canities.

The assignee hereof has identified a means of combating hair whitening by acting on the TRP-2 enzyme (WO 03/103568), especially by increasing the level of GSH. Indeed, it has been demonstrated that the expression of the TRP-2 enzyme is correlated with a higher level of GSH in the melanocytes, the expression of TRP-2 induces an increase in the level of GSH in the melanocytes. Thus, in the melanocytes which do not express TRP-2 (for example, the melanocyte precursors of hair), there is a low level of GSH in comparison with the melanocytes that express the TRP-2 enzyme (for example, all the skin melanocytes).

The assignee hereof has therefore identified a novel target for the treatment of canities, more particularly it has demonstrated that the compounds capable of increasing the level of GSH in the melanocytes that are deficient in TRP-2 increase the viability of these melanocytes, decrease hair whitening and lead, unlike their depigmenting effect described in the literature, to the restoring of hair pigmentation (FR 04/13756).

SUMMARY OF THE INVENTION

It has now been demonstrated that:

coumarin;

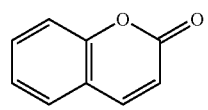 [SMILES: O=c1ccc2ccccc2o1]

and coumarin derivatives, especially 7-isopentenyloxycoumarin;

butylated hydroxyanisole (also denoted by 2-tert-butyl-4-hydroxyanisole and 3-tert-butyl-4-hydroxyanisole);

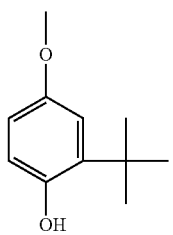

and ethoxyquine (6-ethoxy-2,2,4-trimethyl-1H-quinoline, also called ethoxytrimethyldihydroquinoline), by their ability to increase the level of GSH in the melanocytes, counteract hair whitening and effect the restoring of hair pigmentation.

Thus, the present invention features the administration of at least one compound selected from coumarin and derivatives thereof, butylated hydroxyanisole and ethoxyquine as an agent that prevents, limits or stops the progression of canities, and maintains and/or promotes the natural repigmentation of head hair and/or body hair.

These compounds could also be administered as a mixture.

In particular, the present invention features the administration of at least one compound selected from coumarin and derivatives thereof, butylated hydroxyanisole and ethoxyquine and mixtures thereof to prevent and/or limit and/or stop the development of canities.

This invention also features the administration of at least one compound selected from coumarin and derivatives thereof, butylated hydroxyanisole and ethoxyquine for maintaining the natural pigmentation of grey head hair and/or body hair.

The present invention also features compositions for combating canities, comprising, formulated into a cosmetically acceptable medium, at least one compound selected from coumarin and derivatives thereof, butylated hydroxyanisole and ethoxyquine combined with one other hair active agent selected from agents for combating desquamative conditions of the scalp and/or plant extracts with propigmenting activity.

This invention also features compositions for combating canities comprising, formulated into a cosmetically acceptable medium, at least one compound selected from coumarin and derivatives thereof, butylated hydroxyanisole and ethoxyquine combined with an agent that slows down hair loss or that promotes its regrowth.

Figure 1:
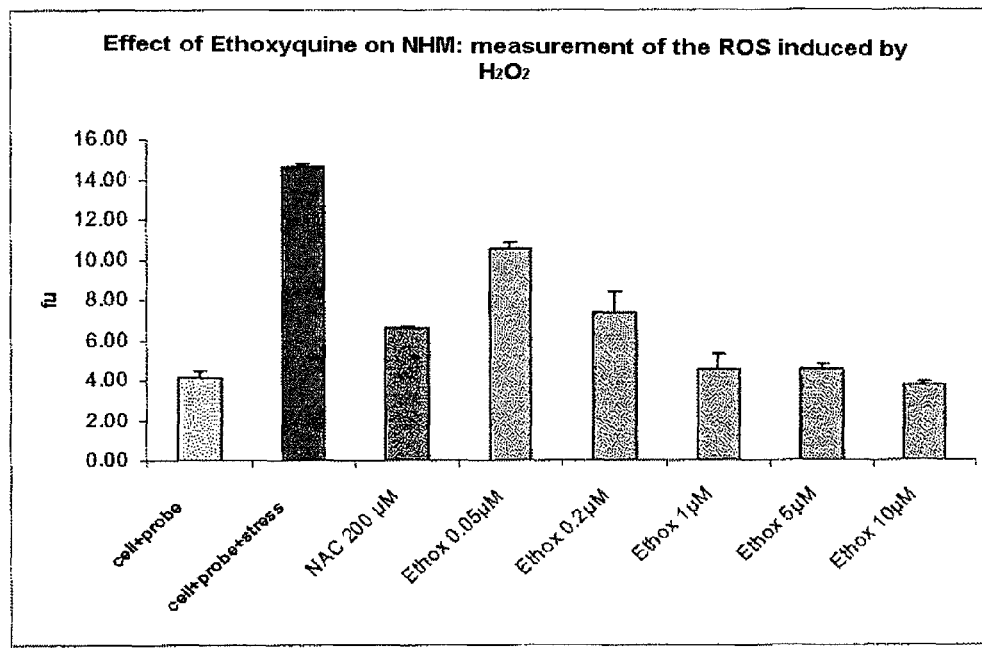
FIG. 1 is a graph showing the effect of ethoxyquine on NHM: measurement of the ROS induced by $H_2O_2$

DETAILED DESCRIPTION OF BEST MODE AND SPECIFIC/PREFERRED EMBODIMENTS OF THE INVENTION

The compositions according to the invention comprise an amount of at least one compound selected from coumarin and derivatives thereof, butylated hydroxyanisole and ethoxyquine of from 0.001% to 10% by weight relative to the total weight of the composition, preferentially from 0.01% to 5% by weight relative to the total weight of the composition and even more preferentially from 0.1% to 1% by weight relative to the total weight of the composition.

The compositions according to the invention may be administered orally or applied topically to the skin (over any cutaneous area of the body covered with hair) and/or the scalp.

Orally, the compositions according to the invention may contain the compound or compounds selected from coumarin and derivatives thereof, butylated hydroxyanisole and ethoxyquine in solution in a dietary liquid such as an optionally flavored aqueous or aqueous-alcoholic solution. They may also be incorporated into an ingestible solid excipient and may be, for example, in the form of granules, pills, tablets or sugar-coated tablets. They may also be dissolved in a dietary liquid that is itself optionally packaged in ingestible capsules.

Depending on the method of administration, whether regime or regimen, the compositions of the invention may be in any galenic form normally used, particularly in cosmetology.

A preferred composition of the invention is a cosmetic composition suitable for topical application to the scalp and/or the skin.

For a topical application, the composition that can be administered according to the invention may especially be in the form of an aqueous, aqueous-alcoholic or oily solution or of a dispersion of the lotion or serum type, of emulsions having a liquid or semi-liquid consistency of the milk type, obtained by dispersion of a fatty phase in an aqueous phase (O/W) or conversely (W/O), or of suspensions or emulsions having a soft consistency of the aqueous or anhydrous cream or gel type, or else of microcapsules or microparticles, or of vesicular dispersions of ionic and/or non-ionic type. It may thus be in the form of an ointment, dye, cream, pomade, powder, patch, impregnated pad, solution, emulsion or vesicular dispersion, lotion, gel, spray, suspension, shampoo, aerosol or foam. They may be anhydrous or aqueous. It may also consist of solid preparations that form soaps or cleansing bars.

These compositions are formulated according to the usual methods.

The composition that is administered according to the invention may, in particular, be a composition for hair care, and especially a shampoo, a setting lotion, a treating lotion, a styling cream or gel, a dye composition (especially oxidation dye compositions) optionally in the form of coloring shampoos, restructuring lotions for the hair, or a mask.

The cosmetic composition according to the invention will preferentially be a cream, hair lotion, shampoo or conditioner.

The amounts of the various constituents of the compositions that are administered according to the invention are those conventionally used in the fields in question.

When the composition according to the invention is an emulsion, the proportion of the fatty phase may range from 5% to 80% by weight, and preferably from 5% to 50% by weight, relative to the total weight of the composition. The oils, waxes, emulsifiers and coemulsifiers included in the composition in the form of an emulsion are selected from those conventionally used in the cosmetics field. The emulsifier and coemulsifier are present in the composition in an amount ranging from 0.3% to 30% by weight, and preferably from 0.5% to 20% by weight, relative to the total weight of the composition. The emulsion may, in addition, contain lipid vesicles.

When the composition according to the invention is an oily gel or solution, the fatty phase may represent more than 90% of the total weight of the composition.

In one embodiment of the invention, the composition will be such that the compound selected from coumarin and derivatives thereof, butylated hydroxyanisole and ethoxyquine is encapsulated in a coating such as microspheres, nanospheres, oleosomes or nanocapsules.

This type of formulation proves advantageous because it makes it possible to specifically target the hair follicle and thus to release the active agent on its site of action.

By way of example, the microspheres can be prepared according to the method described in EP-0,375,520.

The nanospheres can be in the form of an aqueous suspension and be prepared according to the methods described in FR-0015686 and FR-0101438.

Oleosomes consist of an oil-in-water emulsion formed by oily globules provided with a lamellar liquid crystal coating dispersed in an aqueous phase (see EP-0,641,557 and EP-0,705,593).

The compound selected from coumarin and derivatives thereof, butylated hydroxyanisole and ethoxyquine could also be encapsulated in nanocapsules consisting of a lamellar coating obtained from a silicone surfactant (see EP-0,780,115), the nanocapsules can also be prepared based on water-dispersible sulfonic polyesters (see FR-0113337).

The compound selected from coumarin and derivatives thereof, butylated hydroxyanisole and ethoxyquine can also be complexed to the surface of cationic oily globules, regardless of their size (see EP-1,010,413, EP-1,010,414, EP-1,010,415, EP-1,010,416, EP-1,013,338, EP-1,016,453, EP-1,018,363, EP-1,020,219, EP-1,025,898, EP-1,120,101, EP-1,120,102, EP-1,129,684, EP-1,160,005 and EP-1,172,077).

The compound selected from coumarin and derivatives thereof, butylated hydroxyanisole and ethoxyquine may finally be complexed to the surface of nanocapsules or nanoparticles provided with a lamellar coating (see EP-0,447,318 and EP-0,557,489) and containing a cationic surfactant at the surface (see the aforementioned references for the cationic surfactants).

In particular, a composition will be preferred such that the coating containing the compound selected from coumarin and derivatives thereof, butylated hydroxyanisole and ethoxyquine has a diameter of less than or equal to 10 µm. When the coating does not form a spherical vesicle, the diameter is understood to mean the largest dimension of the vesicle.

In a known manner, the compositions according to the invention may also contain adjuvants that are customary in the cosmetics field, such as hydrophilic or lipophilic gelling agents, hydrophilic or lipophilic additives, preservatives, antioxidants, solvents, fragrances, fillers, screening agents, odor absorbers and coloring materials. The amounts of these various adjuvants are those conventionally used in the cosmetics field, and, for example, are from 0.01% to 10% of the total weight of the composition. These adjuvants, depending on their type, may be introduced into the fatty phase, into the aqueous phase and/or into the lipid spherules.

The compositions according to the invention may combine at least one compound selected from coumarin and derivatives thereof, butylated hydroxyanisole and ethoxyquine with other active agents. Among these active agents, exemplary are:

agents modulating the differentiation and/or proliferation and/or pigmentation of skin cells such as retinol and esters thereof, vitamin D and derivatives thereof, oestrogens such as oestradiol, cAMP modulators such as POMC derivatives, adenosine, forskolin and derivatives thereof, prostaglandins and derivatives thereof, triiodothyronine and derivatives thereof;

plant extracts such as those from Iridaceae or soya bean, extracts which may or may not then contain isoflavones;
extracts from microorganisms;

free-radical scavengers such as α-tocopherol or esters thereof, superoxide dismutases or the like, certain metal chelating agents or ascorbic acid and esters thereof;

anti-seborrhoeic agents, such as certain sulfur-containing amino acids, 13-cis-retinoic acid, cyproterone acetate;

other agents for combating the desquamative conditions of the scalp such as zinc pyrithione, selenium disulfide, climbazole, undecylenic acid, ketoconazole, piroctone olamine (octopirox) or ciclopiroctone (ciclopirox);

in particular, they may be active agents that stimulate the regrowth and/or that promote the slowing of hair loss, and more particularly exemplary are:

nicotinic acid esters, especially including tocopheryl nicotinate, benzyl nicotinate and $C_1$-$C_6$ alkyl nicotinates such as methyl or hexyl nicotinates;

pyrimidine derivatives, such as 2,4-diamino-6-piperidinopyrimidine 3-oxide or "Minoxidil" described in U.S. Pat. Nos. 4,139,619 and 4,596,812; Aminexil or 2,4-diaminopyrimidine 3-oxide described in WO 96/09048;

lipoxygenase-inhibiting agents or cyclooxidase-inducing agents that promote hair regrowth such as those described by the assignee hereof in EP-0,648,488;

anti-bacterial agents such as macrolides, pyranosides and tetracyclines, and especially erythromycin;

calcium antagonists, such as cinnarizine, nimodipine and nifedipine;

hormones, such as oestriol or the like, or thyroxine and salts thereof;

anti-androgens, such as oxendolone, spironolactone, diethylstilbestrol and flutamide;

steroid or non-steroid inhibitors of 5-α-reductases, such as those described by the assignee hereof in EP-0,964,852 and EP-1,068,858, or else finasteride;

ATP-dependent potassium channel agonists, such as chromakalim and nicorandil; and plant extracts with propigmenting activity, such as the chrysanthemum extracts as described in FR-2768343 and *Sanguisorba* extracts described in FR-2782920.

Preferably, the compound selected from coumarin and derivatives thereof, butylated hydroxyanisole and ethoxyquine is combined with at least one other hair active agent selected from agents for combating desquamative conditions of the scalp, agents that slow down hair loss or that promote its regrowth, plant extracts with propigmenting activity.

The present invention also features a regime or regimen for the cosmetic treatment of canities, wherein a composition as defined previously comprising at least one compound selected from coumarin and derivatives thereof, butylated hydroxyanisole and ethoxyquine is administered or applied to the area to be treated.

This invention also features a cosmetic treatment regime or regimen useful to maintain the natural pigmentation of grey or white head hair and/or body hair, wherein a composition as defined previously comprising at least one compound selected from coumarin and derivatives thereof, butylated hydroxyanisole and ethoxyquine is administered or applied to the area to be treated.

The methods for treating canities and the pigmentation of grey or white head hair and/or body hair may also entail ingesting a composition comprising at least one compound selected from coumarin and derivatives thereof, butylated hydroxyanisole and ethoxyquine.

The areas to be treated may be, for example, and non-limitingly, the scalp, eyebrows, moustache and/or beard and any area of the skin covered with hair.

More particularly, the methods for the cosmetic treatment of canities and the natural pigmentation of grey or white head hair and/or body hair entails applying a composition comprising at least one compound selected from coumarin and derivatives thereof, butylated hydroxyanisole and ethoxyquine The cosmetic treatment methods for combating canities and/or for maintaining the natural pigmentation of grey or white head hair and/or body hair may, for example, entail applying the composition to the hair and scalp in the evening, keeping the composition on overnight and optionally shampooing in the morning or washing the hair using this composition and again leaving it in contact for a few minutes before rinsing. The compositions according to the invention have proved particularly advantageous when they are applied in the form of an optionally rinse-out hair lotion or even in the form of a shampoo.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Demonstration of the Activity of the Compounds of the Invention

1-A-1. Protocol for Measuring the Reactive Oxygen Species (ROS) Generated by an $H_2O_2$ Stress in Cultured Normal Human Melanocytes (NHM):

The normal human melanocytes (NHMs) were inoculated at D0 at the density of $4\times10^4$ cells/cm$^2$. At D1, the culture medium was replaced with the 10 μM solution of 6-carboxy-2',7'-dichlorodihydrofluorescein diacetate, di[acetoxymethyl ester] in PBS ($H_2$DCFDA, C2938, Molecular Probes). After 20 minutes, the $H_2$DCFDA solution was replaced with the culture medium. The NHMs were left for 30 minutes before adding the $H_2O_2$ solution (250 μM). The fluorescence was measured after 15 minutes in a fluoroscan (excitation: 485 nm, emission: 538 nm).

The compounds studied were used depending on their properties (concentration, preincubation time). N-Acetylcysteine (A9165-Sigma) was used as a reference molecule. The melanocytes were pretreated, 12 h/18 h at 37° C., with the compound studied in the culture medium, before being brought into contact for 20 minutes with $H_2$DCFDA (10 μM in PBS). The $H_2$DCFDA solution was then replaced with the culture medium containing the active agent studied. After incubating for 30 minutes the oxidative stress was induced by addition of 250 μM of $H_2O_2$ in the culture medium. The fluorescence was measured after 15 minutes in a fluoroscan (excitation: 485 nm, emission: 538 nm).

1-A-2. Results:

The results represent the crude fluorescence data, from which the autofluorescence values of "blank" cells, expressed in fluorescence units (fu), obtained during a representative experiment, have been deducted.

The results are given in FIG. 1. A decrease of the reactive oxygen species is indeed observed in the presence of ethoxyquine.

1-B-1. Protocol for Measuring the Viability (Toxicity Control):

The normal human melanocytes (NHMs) were inoculated at D0 at the density of $4\times10^4$ cells/cm$^2$. After adhesion of the cells (3 h), the compound studied was added to the culture medium. After 24 h to 48 h, the cell viability was measured using Alamar Blue (UP669413 UPTIMA, Interchim) according to the instructions of the supplier.

Figure 2:
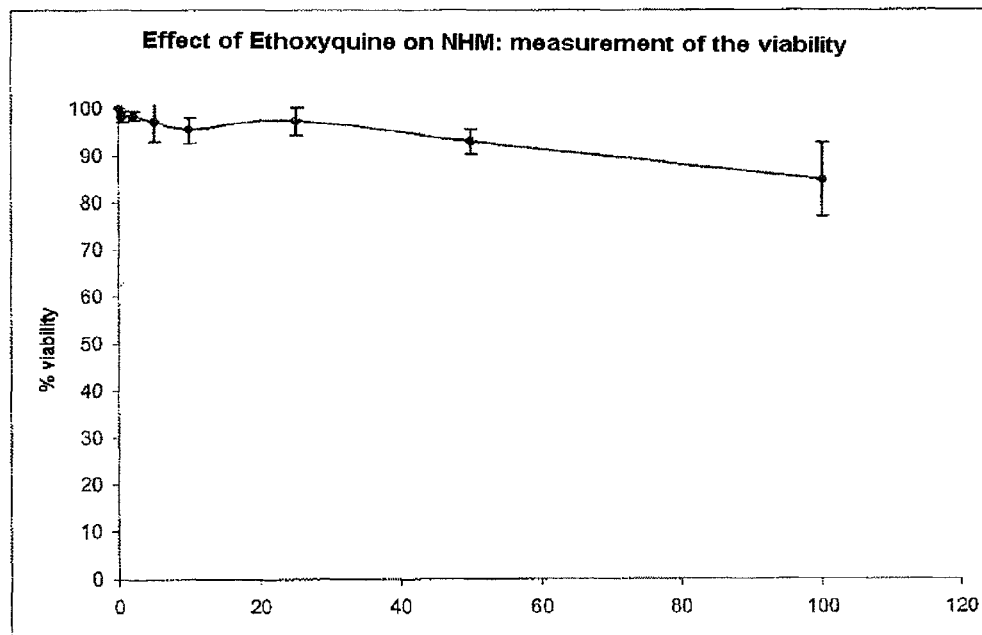
FIG. 2 is a graph showing the effect of ethoxyquine on NHM: measurement of the viability.

1-B-2. Results:

The results represent the fluorescent signal percentages obtained for a representative experiment (measurement in triplicate) (2 independent experiments were carried out) and presented in the form of a % fluorescence curve as a function of the concentration of the active agent studied (in μM). The results are given in FIG. 2.

EXAMPLE 2

Compositions

Hair Lotion:

| | |
|---|---|
| courmarin | 0.5 g |
| propylene glycol | 20 g |
| 95° ethanol | 30 g |
| water | qs for 100 g |

This lotion was applied daily over the areas to be treated and preferably over the entirety of the scalp for at least 10 days and preferentially 1 to 2 months. A decrease in the appearance of white or grey hairs and a repigmentation of the grey hairs was then observed.

Treating Shampoo:

| | |
|---|---|
| butylated hydroxyanisole | 1.5 g |
| polyglyceryl-3 hydroxyaryl ether | 26 g |
| hydroxy propyl cellulose marketed under the trademark KLUCELL G by Hercules | 2 g |
| preservatives | qs |
| 95° ethanol | 50 g |
| water | qs for 100 g |

This shampoo was used at each wash with an exposure time of around one minute. A prolonged use, of around two months, led to the slowing down of canities and to the gradual repigmentation of grey hair.

This shampoo can also be used preventatively in order to delay hair whitening.

Treating Gel:

| | |
|---|---|
| ethoxyquine | 0.75 g |
| essential eucalyptus oils | 1 g |
| econazole | 0.2 g |
| lauryl polyglyceryl-6 cetearyl glycol ether | 1.9 g |
| preservatives | qs |
| CARBOPOL 934P marketed by B F Goodrich Corporation | 0.3 g |
| neutralizing agent | qs pH 7 |
| water | qs for 100 g |

This gel was applied over the areas to be treated twice a day (morning and evening) with a final massage. After applying for three months, a repigmentation of the body hair or head hair of the area treated was observed.

Flexible Gelatin Capsules:

| | |
|---|---|
| coumarin | 0.05 g/ |
| capsule excipient | qs |

Three capsules can be taken per day.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic composition useful for limiting the development of canities in a subject in need of such treatment, comprising a thus effective amount of an admixture of coumarin, butylated hydroxyanisole, and ethoxyquine, and at least one other active agent selected from the group consisting of active agents for combating desquamative conditions of the scalp, plant extracts having propigmenting activity, and mixtures thereof, formulated into a cosmetically acceptable medium therefor, wherein said admixture is encapsulated in a coating of microspheres, nanospheres, oleosomes or nanocapsules.

2. A cosmetic composition useful for limiting the development of canities in a subject in need of such treatment, comprising a thus effective amount of an admixture of coumarin, butylated hydroxyanisole, and ethoxyquine, and at least one other active agent selected from the group consisting of active agents that slow hair loss, promote hair regrowth, and mixtures thereof, formulated into a cosmetically acceptable medium therefor, wherein said admixture is encapsulated in a coating of microspheres, nanospheres, oleosomes or nanocapsules.

3. The cosmetic composition as defined by claim 1, formulated into a topically applicable, cosmetically acceptable medium therefor.

4. The cosmetic composition as defined by claim 2, formulated into a topically applicable, cosmetically acceptable medium therefor.

5. The cosmetic composition according to claim 1 or claim 2, wherein said coumarin, butylated hydroxyanisole, and ethoxyquine mixture is present in an amount from 0.001% to 10% by weight relative to the total weight of the composition.

6. The cosmetic composition according to claim 1 or claim 2, wherein said composition is formulated for administration orally, topically to the skin, topically to any cutaneous area covered with hair, and/or topically to the scalp.

7. The cosmetic composition according to claim 1 or claim 2, wherein said admixture is contained in a vesicle whose diameter is less than or equal to 10 μm.

* * * * *